United States Patent [19]

Finizio

[11] Patent Number: 4,548,946
[45] Date of Patent: Oct. 22, 1985

[54] ANTIINFLAMMATORY AND/OR ANALGESIC 1,8-DIHYDRO-(OR 3,8-DIHYDRO)-8-ARYL-2-[(SUBSTITUTED)-THIO]-INDENO[1,2-D]IMIDAZOLES AND THEIR CORRESPONDING SULFOXIDES AND SULFONES

[75] Inventor: Michael Finizio, Wilmington, Del.

[73] Assignee: E. I. Du Pont de Nemours and Company, Wilmington, Del.

[21] Appl. No.: 349,201

[22] Filed: Feb. 22, 1982

Related U.S. Application Data

[63] Continuation-in-part of Ser. No. 248,010, Mar. 26, 1981, abandoned.

[51] Int. Cl.[4] .................. A61K 31/415; C07D 235/02
[52] U.S. Cl. .................................... 514/393; 514/338; 546/271; 548/323
[58] Field of Search .................. 548/323; 546/271; 424/273 R, 263; 514/338, 393

[56] References Cited

U.S. PATENT DOCUMENTS 3,792,057  2/1974  Jensen et al. ..................... 548/323

OTHER PUBLICATIONS

Hansch, C., et al. *J. Med. Chem.*, 16(11), 1207, (1973).
Von Heinz, P., et al. *J. Prakt. Chem.*, 28 (5–6), 297–304, (1965).
March, J., *Advanced Organic Chemistry*, McGraw Hill, New York, 1968, pp. 328 and 887.
Hofmann, K., *Imidazole and its Derivatives*, Part I, Interscience, New York, 1953, p. 49.

Primary Examiner—Richard A. Schwartz

[57] ABSTRACT 1,8-Dihydro(or 3,8-dihydro)-8-aryl-2-[(substituted)thio]indeno[1,2-d]imidazoles and their corresponding sulfoxides and sulfones, such as 1,8-dihydro(or 3,8-dihydro)-8-phenyl-2-[(1,1,2,2-tetrafluoroethyl)sulfonyl]indeno[1,2-d]imidazole, are useful in the treatment of inflammation and/or pain.

15 Claims, No Drawings

ANTIINFLAMMATORY AND/OR ANALGESIC 1,8-DIHYDRO-(OR 3,8-DIHYDRO)-8-ARYL-2-[(SUBSTITUTED)THIO]-INDENO[1,2-D]IMIDAZOLES AND THEIR CORRESPONDING SULFOXIDES AND SULFONES

RELATIONSHIP TO OTHER APPLICATIONS

This application is a continuation-in-part of application Ser. No. 248,010, filed Mar. 26, 1981, now abandoned.

FIELD OF INVENTION

This invention relates to indenoimidazoles, their preparation, pharmaceutical compositions containing them and methods of using them to treat inflammation and/or pain in mammals. More particularly, this invention relates to antiinflammatory and/or analgesic 1,8-dihydro(or 3,8-dihydro)-8-aryl-2-[(substituted)thio]indeno[1,2-d]imidazoles and their corresponding sulfoxides and sulfones.

PRIOR ART

H. Paul and K. Walter, *J. Prakt. Chem.*, 28 (5-6), 297–304 (1965) describe a compound of the formula:

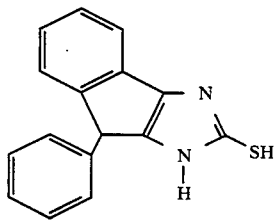

However, no biological activity is reported.

There is a continuing need for safe and effective antiinflammatory agents. Inflammation is a disease process characterized by redness, fever, swelling, and pain. Arthritis, in its various forms, is the most prevalent, chronic and severe of the inflammatory diseases. Traumatic injury and infection also involve inflammation, and antiinflammatory drugs are often used in their treatment. The usefulness of most commercial antiinflammatories is limited because of toxicity and adverse side-effects. Many produce gastric irritation and other effects, such as changes in blood cells and central nervous system. Adrenocortical steroids produce gastric irritation and suppression of normal adrenal function.

The present invention results from efforts to develop new anti-arthritic compounds with good antiinflammatory activity and minimal side effects that could be more effective in treating arthritis than presently available drugs.

In addition to antiinflammatory properties, some compounds of this invention have demonstrated analgesic activity in a test procedure. This additional property is desirable in treatment of arthritis or related diseases; however, such compounds can be employed solely to alleviate pain.

SUMMARY OF THE INVENTION

According to the invention, there is provided a compound of the formula:

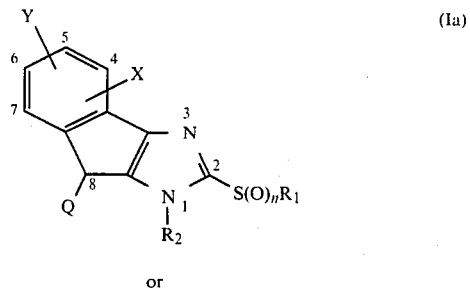

or

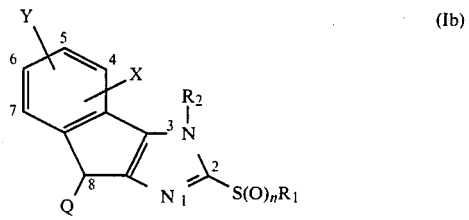

where
Q is

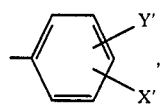

pyridyl or thienyl;
n is 0, 1 or 2;
$R_1$ is alkyl of 1 or 2 carbon atoms, or mono- or polyhaloalkyl of 1 or 2 carbon atoms;
$R_2$ is H, $C_1$-$C_6$ alkyl,

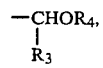

2-tetrahydropyranyl, 2-tetrahydrofuranyl, 4-nitrobenzyl, —$COOR_5$, —$COR_5$, —COAr or —$SO_2$Ar
where
$R_3$ is H or methyl;
$R_4$ is alkyl of 1–2 carbon atoms, benzyl, —$CH_2CH_2OCH_3$ or —$COR_5$;
$R_5$ is alkyl of 1–4 carbon atoms, or benzyl;
Ar is

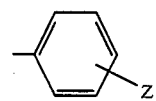

where Z is H, F, Cl, Br, alkyl of 1–4 carbon atoms, alkoxy of 1–4 carbon atoms or nitro; with the proviso that when $R_2$ is 4-nitrobenzyl, n is 2 and when $R_2$ is —$COOR_5$, —$COR_5$, —COAr or —$SO_2$Ar, n is 0;
X, Y, X' and Y' are independently H, F, Cl, Br, $NO_2$, alkoxy of 1 or 2 carbon atoms, —N($C_{1-2}$ alkyl)$_2$, alkyl of 1 or 2 carbon atoms, —S(O)$_m$$C_{1-2}$ alkyl where m is 0, 1 or 2; or
a pharmaceutically suitable acid addition salt thereof when n is 0 or when X, Y, X' or Y' is —N($C_{1-2}$ alkyl)$_2$ or when Q is pyridyl; or a pharmaceutically suitable metal salt thereof when n is 1 or 2 and $R_2=H$.

When $R_2=H$ structures of the type (Ia) and (Ib) are tautomers.

Moreover, compounds of the type (Ia) and (Ib) have an asymmetric center (carbon 8). This invention is intended to include the d form, the l form and the dl racemic mixture of each compound. Resolution of these compounds can be carried out by standard techniques.

There is also provided a process for preparing the aforesaid compounds which comprises:

(a) contacting a compound of the formula:

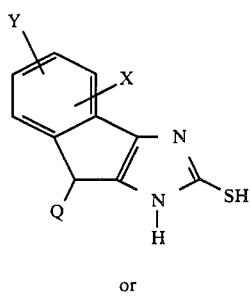

or

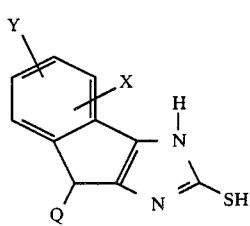

wherein Q, X and Y are as defined above, with an alkylating agent suitable to introduce an $R_1$ group, and (b) optionally contacting the resulting compound with an oxidizing agent; and (c) optionally contacting a compound from step (a) or step (b) with an alkylating, acylating or sulfonylating agent suitable to introduce an $R_2$ group other than H.

Also provided are pharmaceutical compositions containing at least one of the aforesaid compounds and methods of using them to treat inflammation and/or alleviate pain in mammals.

PREFERRED SCOPE

Compounds of preferred scope are those of the formula:

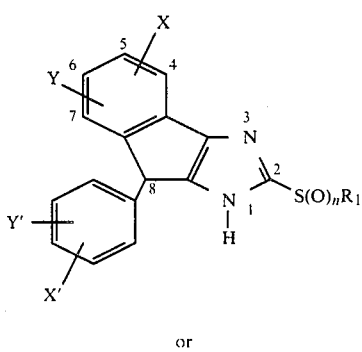

or

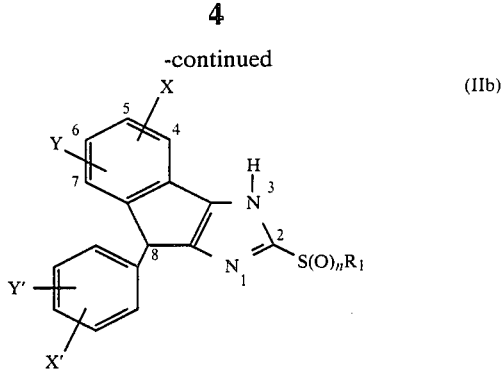

where n, X, Y, X' and Y' are as defined previously and $R_1$ is alkyl of 1 or 2 carbons or mono- or poly-fluoroalkyl of 1 or 2 carbons.

More preferred are compounds of Formula (IIa) or (IIb) wherein:

n is 0 or 2; or $R_1$ is $-CF_3$ or $-CF_2CHF_2$; or

X, Y, X' and Y' are independently H, F, Cl, $-OCH_3$ or $-CH_3$.

Most preferred are those compounds of the more preferred type, but where the substituent in the 4-position is H.

Specifically preferred are compounds of Formula (IIa) or (IIb) where:

n is 0 or 2;

$R_1$ is $-CF_3$ or $-CF_2CF_2H$; and

X, Y, X' and Y' are H.

PHARMACEUTICAL SALTS

Pharmaceutically suitable salts and their preparation are well known to those skilled in pharmaceuticals and any can be used in the present invention. Suitable salts of compounds where n is 0 or when X, X', Y or Y' is $-N(C_{1-2}\ alkyl)_2$ or when Q is pyridyl include pharmaceutically suitable acid addition salts, preferably formed from mineral acids, and include hydrochloride, nitrate and sulfate. The acid used preferably has a $pK_a$ of not greater than 2.5.

Pharmaceutically suitable salts of compounds where n is 1 or 2 and $R_2$ is H include alkali metals and alkaline earth metals such as sodium, potassium and calcium.

SYNTHESIS

The compounds of this invention can be prepared from 1,8-dihydro(or 3,8-dihydro)-8-aryl-indeno[1,2-d]imidazole-2-thiols. The synthesis of the latter compounds involves conversion of the properly substituted ketones to the corresponding tosyloximes; these in turn are subjected to Neber rearrangement [P. W. Neber and A. Friedolsheim, Ann., 449, 109 (1926)] and produce 2-amino-3-aryl-1-indanone hydrochlorides which, upon treatment with potassium thiocyanate, give 1,8-dihydro(or 3,8-dihydro)-8-aryl-indeno[1,2-d]imidazole-2-thiols (Scheme I).

Scheme I

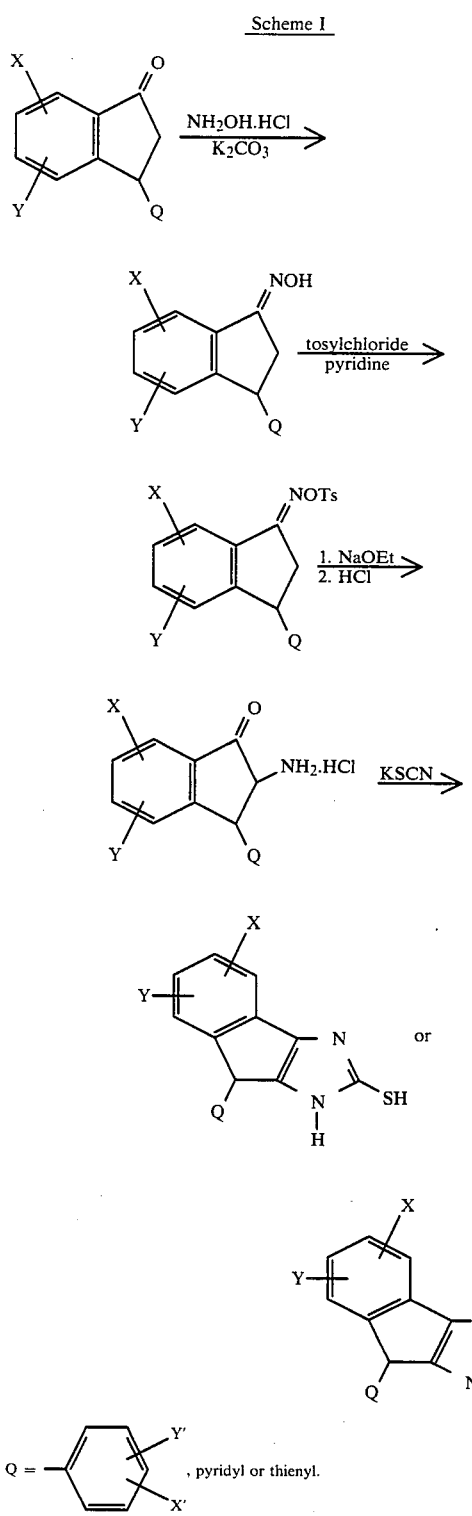

Preparation of the starting ketones can be accomplished by cyclization of the corresponding β,β-diaryl-propionic acids with a strong acid such as aluminum chloride, sulfuric acid, polyphosphoric acid, or hydrofluoric acid (Scheme II).

Scheme II

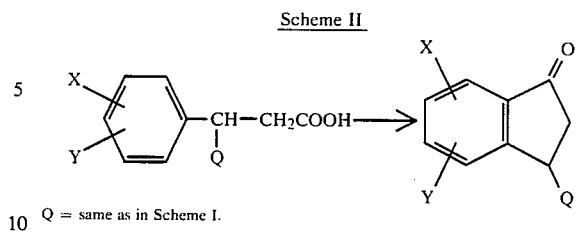

Q = same as in Scheme I.

Q=same as in Scheme I.

Alternatively, the ketones may be prepared by reaction of an indan-1,3-dione with an aryl lithium or aryl magnesium halide reagent to give a β-hydroxy ketone which is reduced either catalytically with palladium on charcoal at 1 atmosphere of hydrogen or with boron trifluoride/trialkyl silane to give the ketones of Scheme I.

The sequence illustrated in Scheme I is similar to the one reported by D. Huckle, I. M. Lockhart and M. Wright, *J. Med. Chem.*, 12(3), 277-79 (1969) for the preparation of 3-amino-4-chromanones.

The 2-amino-1-indanones of Scheme I can also be prepared by conversion of the ketones into isonitroso ketones (*Org. Syn., II*, 363) and catalytic reduction of the latter [S. Kimoto et al., *Yakugaku Zasshi*, 88 (10), 1323-8, (1968)], (Scheme III).

Scheme III

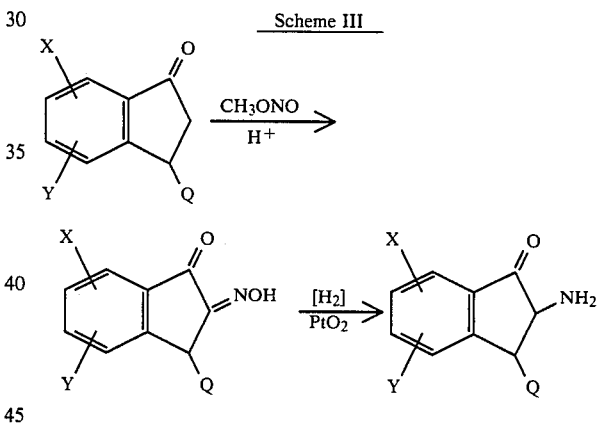

Q=same as in Scheme I

The appropriate R₁ group can be introduced by alkylating the 1,8-dihydro(or 3,8-dihydro)-8-arylindeno[1,2-d]imidazole-2-thiols with a suitable alkylating agent such as ethyl iodide or 2,2,2-trifluoroethyl trichloromethanesulfonate. Also, the 1,8-dihydro(or 3,8-dihydro)-8-aryl-indeno[1,2-d]imidazole-2-thiols can be reacted with tetrafluoroethylene to provide 2-[(1,1,2,2-tetrafluoroethyl)thio] derivatives. Similar addition reactions of tetrafluoroethylene and other fluorinated olefins are described in England, D. C. et al., *J. Am. Chem. Soc.*, 82, 5116 (1960) and Rapp, K. E., et al, *J. Am. Chem. Soc.*, 72, 3642 (1950). For the purpose of this disclosure tetrafluoroethylene and other fluorinated olefins used are considered alkylating agents.

Compounds where R₁=CF₃ are preferably prepared by irradiating a mixture of the thiol and trifluoromethyl iodide as alkylating agent in liquid ammonia. An inert solvent such as ether, tetrahydrofuran or the like is usually added in order to have a homogeneous solution.

The 1,8-dihydro(or 3,8-dihydro)-8-aryl-2-[(substituted)thio]indeno[1,2-d]imidazoles can then be oxidized to the corresponding sulfoxides or sulfones by using oxidizing agents such as m-chloroperbenzoic acid, [Tweit, R. C., et al., *J. Med. Chem.*, 16, 1161 (1973)]; sodium metaperiodate, [Leonard, N. J. and Johnson, C. R., *J. Org. Chem.*, 27, 282 (1962)]; hydrogen peroxide, [Kochergin, P. M. and Shchukina, M. N., *J. Gen. Chem. U.S.S.R.*, 25, 2289 (1955)], or potassium permanganate, Rapp, K. E., et al., loc. cit.

Compounds of Formula (Ia) or (Ib) of this invention with $R_2$ other than H can be prepared by alkylation, acylation or sulfonylation of the corresponding compounds with $R_2$=H. These reactions can be conducted in the presence or absence of a base, such as potassium carbonate, pyridine, triethylamine, potassium t-butoxide, sodium hydride and the like. Examples of alkylating, acylating and sulfonylating agents capable of introducing other $R_2$ groups are methyl iodide, 2-chlorotetrahydrofuran, 4-nitrobenzyl chloride, acetic anhydride, acetyl chloride, ethyl chloroformate, benzoyl chloride and benzenesulfonyl chloride and the like. Generally, a halide of an appropriate $R_2$ group, preferably a chloride, is used to introduce the $R_2$ group other than hydrogen. In the following examples, temperatures are in degrees centigrade.

PREPARATION OF INTERMEDIATES

3-(3-Methoxyphenyl)-3-hydroxyindan-1-one m-Methoxyphenyl magnesium bromide (prepared from 10 g of the corresponding bromide and 1.45 g of magnesium turnings in ether) was treated at 0° with a solution of 1,3-indandione (3.5 g) in ether. After stirring at 25° for 4.5 hours, the mixture was quenched with saturated ammonium chloride solution. The layers were separated, the aqueous layer was extracted with ether, and the organic layers were dried (MgSO₄) and concentrated. Chromatography of the residue on silica gel provided the title compound as a viscous yellow oil (3.6 g, 59%). NMR and IR spectra were consistent with the assigned structure.

3-(3-Methoxyphenyl)indan-1-one

A solution of 3-(3-methoxyphenyl)-3-hydroxyindan-1-one (2.3 g) in 25 ml methylene chloride was stirred at 0°, then treated sequentially with 1.6 ml triethylsilane and 3.3 ml of boron trifluoride etherate. The mixture was warmed to 25° and stirred for 16 hours, then diluted with water and extracted with additional methylene chloride. After drying (MgSO₄) and concentration, the residue was chromatographed on silica gel to provide the title compound as a light yellow oil (0.5 g, 23%). NMR and IR spectra were consistent with the assigned structure.

2,3-Dihydro-1-(hydroxyimino)-3-phenyl-1H-indene

A mixture of 3-phenylindan-1-one (80 g), methanol (935 ml), water (90 ml), potassium carbonate (103.8 g), and hydroxylamine HCl (104.3 g) was heated at reflux for 16 hours, then poured into ice-water: the title compound was filtered, washed with water, with a small portion of ether, then dried in air. Yield: 74.7 g; m.p. 133°–139°.

2,3-Dihydro-1-[(4-methylphenyl)sulfonyloximino]-3-phenyl-1H-indene

A solution of p-toluenesulfonyl chloride (102.2 g) in pyridine (140 ml) was added dropwise at 5°–10° to 2,3-dihydro-1-(hydroxyimino)-3-phenyl-1H-indene (60 g) in 270 ml pyridine. The reaction mixture was then stirred for 8 hours at room temperature, poured into ice-water to separate out the title compound, which was filtered, washed several times with water, then once with ether, and finally dried in air. Yield: 96.5 g; m.p. 123°–127°.

2-Amino-2,3-dihydro-3-phenyl-1H-inden-1-one Hydrochloride

A solution of sodium ethoxide in ethanol (from 6.4 g of sodium and 350 ml of ethanol) was added dropwise at 0°–5° to 2,3-dihydro-1-[(4-methylphenyl)sulfonyloximino]-3-phenyl-1H-indene (96.5 g) in 1500 ml of toluene. The reaction mixture was stirred at room temperature under nitrogen for 24 hours, filtered through Celite, washed with water and extracted with 1N HCl. The combined acidic extracts were washed with ether, rotoevaporated and the residue was triturated with acetone to give the title compound. Yield: 18.0 g; m.p. 298°(dec.).

1,8-Dihydro(or 3,8-dihydro)-8-phenyl-indeno[1,2-d]-imidazole-2-thiol

A mixture of 2-amino-2,3-dihydro-3-phenyl-1H-inden-1-one HCl (10.4 g), acetic acid (45 ml) and potassium thiocyanate (4.8 g) was heated at reflux for 25 minutes. After cooling, a solid product was filtered off and washed with water to give the title compound. Yield 9.6 g; m.p. 260°–265° (dec.).

EXAMPLE 1

1,8-Dihydro(or 3,8-dihydro)-2-[(1,1,2,2-tetrafluoroethyl)thio]-8-phenyl-indeno[1,2-d]imidazole To a stainless steel tube was added 1,8-dihydro(or 3,8-dihydro)-8-phenyl-indeno[1,2-d]imidazole-2-thiol (10 g,), dimethylformamide (240 ml) and diisopropylamine (3.8 g). Subsequent to purging the tube several times with dry nitrogen, tetrafluoroethylene (4.2 g) was introduced. The tube was agitated at 50° for 8 hours. The reaction mixture was poured into water and extracted with ethyl acetate. The organic phase was dried over magnesium sulfate and rotoevaporated. The resulting crude product was purified through a silica gel column (toluene-ethyl acetate 9:1 as eluent). Yield 7.4 g; m.p. 213°–215° (dec.).

EXAMPLE 2

1,8-Dihydro(or 3,8-dihydro)-2-[(1,1,2,2-tetrafluoroethyl)sulfonyl]-8-phenyl-indeno[1,2-d]imidazole To a solution of 1,8-dihydro(or 3,8-dihydro)-2-[(1,1,2,2-tetrafluoroethyl)thio]-8-phenyl-indeno[1,2-d]imidazole (3.6 g) in ethyl acetate (60 ml) was added portionwise 86.4% m-chloroperbenzoic acid (4.5 g). The mixture was stirred for 24 hours at room temperature, additional m-chloroperbenzoic acid (2.7 g) was added, and stirring at room temperature was continued for 5 more hours. The mixture was then washed with 10% sodium sulfite, 10% sodium bicarbonate, and finally dried with magnesium sulfate and concentrated on a rotary evaporator. The resulting product was chromatographed through silica gel (toluene-ethyl acetate 9:1 as eluent) to give the title compound. Yield: 3.0 g; m.p. 282°–283° (dec.).

EXAMPLE 3

1,8-Dihydro(or 3,8-dihydro)-2-[(trifluoromethyl)thio]-8-phenyl-indeno[1,2-d]imidazole Liquid ammonia (125 ml) was condensed in a flask provided with dry-ice condenser and containing 1,8-dihydro(or 3,8-dihydro)-8-phenyl-indeno[1,2-d]imidazole-2-thiol (4 g) and tetrahydrofuran (50 ml) was added to obtain a homogeneous solution. This mixture was cooled to −78° and treated with trifluoromethyl iodide (2.5 ml) added slowly as a gas. When the addition was completed the cooling bath was removed and the reaction mixture was irradiated for 4 hours with a General Electric 275 W sun lamp. The ammonia was then allowed to evaporate, the solvent was stripped on a roto-evaporator and the resulting residue washed with water and recrystallized from toluene. Yield: 6 g; m.p. 212°–216° (dec.).

EXAMPLE 4

1,8-Dihydro(or 3,8-dihydro)-2-[(trifluoromethyl)sulfonyl]-8-phenyl-indeno[1,2-d]imidazole To a solution of 1,8-dihydro(or 3,8-dihydro)-2-[(trifluoromethyl)thio]-8-phenyl-indeno[1,2-d]imidazole (4 g) in ethyl acetate (65 ml) was added portionwise 86.4% m-chloroperbenzoic acid (4.5 g). The mixture was stirred at room temperature for 3 days, then washed with 10% sodium sulfite, 10% sodium bicarbonate. The organic phase was dried over magnesium sulfate, concentrated and chromatographed through silica gel (toluene-ethyl acetate 9:1 as eluent) to obtain the title compound. Yield: 1.0 g; m.p. 275°–279° (dec.).

EXAMPLE 5

1,8-Dihydro(or 3,8-dihydro)-2-[(trifluoromethyl)sulfinyl]-8-phenyl-indeno[1,2-d]imidazole The title compound was obtained as a side product in the reaction described in Example 4 and was separated by chromatography (conditions described in Example 4), m.p. 210°–212° (dec.).

EXAMPLE 6

1,8-Dihydro(or 3,8-dihydro)-2-(methylthio)-8-phenyl-indeno[1,2-d]imidazole

A mixture of 1,8-dihydro(or 3,8-dihydro)-8-phenyl-indeno[1,2-d]imidazole-2-thiol (7.9 g), ethanol (150 ml) and iodomethane (4.68 g) was heated at reflux for 2 hours. The reaction mixture was cooled and the title compound was filtered off. Yield 6.5 g: m.p. 241°–245° (dec.).

EXAMPLE 7

1,8-Dihydro(or 3,8-dihydro)-2-(methylsulfonyl)-8-phenyl-indeno[1,2]-dimidazole To a solution of 1,8-dihydro(or 3,8-dihydro)-2-(methylthio)-8-phenyl-indeno[1,2-d]imidazole (4.1 g) in ethyl acetate (100 ml) was added portionwise 86.4% m-chloroperbenzoic acid (5.5 g). This mixture was stirred overnight at room temperature, then washed with 10% sodium sulfite, 10% sodium bicarbonate, dried over magnesium sulfate, concentrated on a roto-evaporator and chromatographed through silica gel (toluene-ethyl acetate 9:1 as eluent) to give the title compound. Yield: 1 g; m.p. 236° (dec.).

Other 1,8-dihydro(or 3,8-dihydro)-2-[(substituted)thio]-8-phenyl-indeno[1,2-d]imidazoles and their corresponding sulfones that were prepared by the procedures described in the above examples are given in Table I.

TABLE I

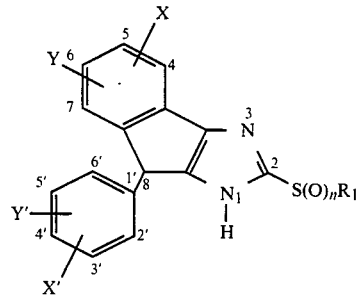

or

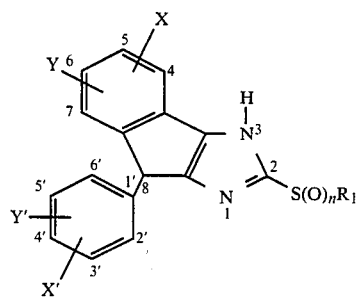

| Ex. | X,Y,X'Y' | $R_1$ | n | m.p. (°C.) | Yield (%) |
|---|---|---|---|---|---|
| 1 | H | $CF_2CHF_2$ | 0 | 213–215° (dec) | 54 |
| 2 | H | $CF_2CHF_2$ | 2 | 282–283° (dec) | 77 |
| 3 | H | $CF_3$ | 0 | 212–216° (dec) | 60 |
| 4 | H | $CF_3$ | 2 | 275–279° (dec) | 20 |
| 5 | H | $CF_3$ | 1 | 210–212° (dec) | *a |
| 6 | H | $CH_3$ | 0 | 241–245° (dec) | 86 |
| 7 | H | $CH_3$ | 2 | 236° (dec) | 20 |
| 8 | 6-$OCH_3$ | $CF_3$ | 0 | 230–233° | 78 |
| 9 | 4-$OCH_3$ | $CF_3$ | 0 | 118–125° | 25 |
| 10 | 3',4'-di-Cl | $CF_3$ | 0 | 163–166° | 16 |
| 11 | H | $CH_2CH_3$ | 0 | 205–214 (D) | 68 |
| 12 | H | $(CH_2)_3CH_3$ | 0 | 194–197 (D) | 94 |
| 13 | 4'-$OCH_3$ | $CF_3$ | 0 | 120–135° | 60 |
| 14 | 4'-$OCH_3$ | $CF_3$ | 2 | 217–218° | 45 |
| 15 | 5-$CH_3$ | $CF_2CHF_2$ | 0 | 192–193° | 47 |
| 16 | 5-$CH_3$ | $CF_2CHF_2$ | 2 | 223–225° | 48 |
| 17 | 4'-F | $CF_3$ | 0 | 231° (D) | 19 |
| 18 | 4'-$SO_2CH_3$ | $CF_2CHF_2$ | 0 | | |
| 19 | 4'-$SO_2CH_3$ | $CF_2CHF_2$ | 2 | | |
| 20 | 4'-$N(CH_3)_2$ | $CF_2CHF_2$ | 0 | * | |
| 21 | 2'-$OCH_3$ | $(CH_2)_3CH_3$ | 0 | ** | |
| 22 | 3'-$NO_2$ | $(CH_2)_3CH_3$ | 0 | | |
| 23 | 3'-$OCH_3$ | $CH_3$ | 0 | | |

*a side product of Example 4
*oil; Mass spectrum m/e 375 (M+)
**oil; Mass spectrum m/e 350 (M+)

Following the procedures described, the following 1,8-dihydro(or 3,8-dihydro)-2-[(substituted)thio]-8-arylindeno[1,2-d]imidazoles and their corresponding sulfoxides and sulfones can be prepared (Table II).

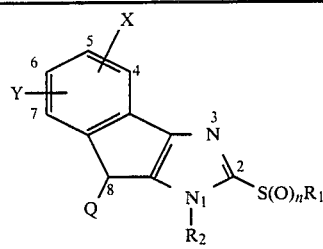

or

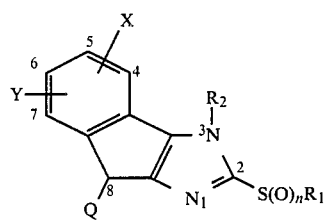

| Ex. | Q | X,Y | n | R₁ | R₂ |
|---|---|---|---|---|---|
| 24 | 4'-CH$_3$OC$_6$H$_4$ | H | 0 | CF$_2$CHF$_2$ | —SO$_2$C$_6$H$_5$ |
| 25 | 4'-CH$_3$OC$_6$H$_4$ | 5-CH$_3$O | 0 | CF$_3$ | H |
| 26 | 3'-CH$_3$OC$_6$H$_4$ | 5-CH$_3$O | 2 | CF$_3$ | H |
| 27 | 3',4'-dichloro-C$_6$H$_3$ | H | 2 | CF$_2$CHF$_2$ | 4-NO$_2$C$_6$H$_4$CH$_2$— |
| 28 | 4'-ClC$_6$H$_4$ | 5-Cl | 0 | CF$_3$ | 2-tetrahydropyranyl |
| 29 | 4'-CH$_3$SC$_6$H$_4$ | H | 0 | CF$_2$CHF$_2$ | H |
| 30 | 3-pyridyl | H | 0 | CF$_3$ | H |
| 31 | 2-thienyl | H | 0 | CF$_3$ | H |
| 32 | C$_6$H$_5$ | 6-Cl | 0 | CF$_2$CHF$_2$ | —COC$_6$H$_5$ |
| 33 | 4'-CH$_3$C$_6$H$_4$ | H | 2 | CF$_3$ | H |
| 34 | C$_6$H$_5$ | 4,7-dimethyl | 0 | CF$_2$CHF$_2$ | H |
| 35 | C$_6$H$_5$ | 6-(CH$_3$)$_2$N | 0 | CH$_2$CHF$_2$ | H |
| 36 | 4'-FC$_6$H$_4$ | H | 0 | CF$_3$ | 2-tetrahydrofuranyl |
| 37 | 3,4-dimethoxy-C$_6$H$_3$ | 5,6-dimethoxy | 0 | CF$_3$ | H |
| 38 | C$_6$H$_5$ | 6-C$_2$H$_5$O | 2 | CH$_2$CH$_3$ | H |
| 39 | 4'-CH$_3$OC$_6$H$_4$ | H | 0 | CH$_2$CF$_3$ | —SO$_2$C$_6$H$_5$ |
| 40 | 4'-CH$_3$OC$_6$H$_4$ | H | 2 | CF$_2$CH$_2$F | H |
| 41 | 4'-FC$_6$H$_4$ | 6-OCH$_3$ | 2 | CF$_3$ | H |
| 42 | 4'-FC$_6$H$_4$ | 6-OCH$_3$ | 2 | CHF$_2$ | H |
| 43 | 4'-CH$_3$SO$_2$C$_6$H$_4$ | H | 0 | CF$_2$CHF$_2$ | H |
| 44 | 4'-NO$_2$C$_6$H$_4$ | H | 0 | CF$_3$ | H |
| 45 | C$_6$H$_5$ | H | 0 | CF$_2$CHF$_2$ | —C(O)CH$_3$ |
| 46 | C$_6$H$_5$ | H | 0 | CF$_2$CHF$_2$ | COOCH$_3$ |
| 47 | 4'-CH$_3$OC$_6$H$_4$ | 6-CH$_3$O | 2 | CF$_3$ | H |
| 48 | 4'-BrC$_6$H$_4$ | H | 2 | CF$_3$ | H |
| 49 | 4'-(CH$_3$CH$_2$)$_2$NC$_6$H$_4$ | H | 0 | CF$_2$CHF$_2$ | H |
| 50 | C$_6$H$_5$ | 6-CH$_3$CH$_2$ | 0 | CF$_3$ | H |
| 51 | C$_6$H$_5$ | H | 0 | CF$_3$ | CH(CH$_3$)OCH$_2$CH$_3$ |
| 52 | C$_6$H$_5$ | H | 0 | CF$_2$CHFBr | H |
| 53 | C$_6$H$_5$ | H | 0 | CF$_2$CHFCl | H |
| 54 | C$_6$H$_5$ | H | 2 | CF$_3$ | CH$_3$ |
| 55 | C$_6$H$_5$ | H | 2 | CF$_3$ | (CH$_2$)$_5$CH$_3$ |
| 56 | C$_6$H$_5$ | H | 0 | CF$_3$ | CH$_3$ |
| 57 | 3'-CH$_3$OC$_6$H$_4$ | 6-CH$_3$O | 0 | CF$_2$CHF$_2$ | H |
| 58 | 4'-CH$_3$OC$_6$H$_4$ | 5-CH$_3$O | 0 | CF$_2$CHF$_2$ | H |
| 59 | 3-thienyl | H | 0 | CF$_2$CHF$_2$ | H |

DOSAGE FORMS

The antiinflammatory and/or analgesic agents of this invention can be administered to treat inflammation and/or relieve pain by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 25 milligrams per kilogram per day given in divided doses 1 to 6 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl or propyl-paraben, and chlorobutanol.

Suitable pharmaceutical carriers are described in *Remington's Pharmaceutical Sciences*, E. W. Martin, a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 75 milligrams of powdered active ingredient, 150 milligrams of lactose, 24 milligrams of talc, and 6 milligrams magnesium stearate.

SOFT GELATIN CAPSULES

A mixture of active ingredient in soybean oil is prepared and injected by means of a positive displacement pump into gelatin to form soft gelatin capsules containing 75 milligrams of the active ingredient. The capsules are washed in petroleum ether and dried.

TABLETS

A large number of tablets are prepared by conventional procedures so that the dosage unit is 75 milligrams of active ingredient, 6 milligrams of magnesium stearate, 70 milligrams of microcrystalline cellulose, 11 milligrams of cornstarch and 200 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is sterilized by commonly used techniques.

SUSPENSION

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

INJECTABLE

A parenteral composition suitable for administration by injection is prepared by dissolving 1% by weight of active ingredient in sodium chloride injection U.S.P. XX and adjusting the pH of the solution to between 6 and 7. The solution is sterilized by commonly used techniques.

USE

To detect and compare the antiinflammatory activities of compounds in this series and standard drugs, a test was used based on a standard model of arthritis for which there is good correlation with human efficacy. The model is adjuvant-induced arthritis in rats. *Federation Proceedings*, Vol. 32, No. 2, 1973 "Models Used for the Study and Therapy of Rheumatoid Arthritis''—Symposium of the American Society for Pharmacology and Experimental Therapeutics—states "The rat polyarthritis produced by intradermal injection of a suspension of *Mycobacterium tuberculosis* in mineral oil (adjuvant) has been used extensively for the screening of drugs of potential use in rheumatoid arthritis."

ESTABLISHED ADJUVANT-INDUCED ARTHRITIS IN RATS

Charles River Lewis male rats (130-150 grams) are injected subcutaneously in the plantar area of the right hind paw with 0.1 ml of adjuvant (Difco heat-killed, lyophilized *Mycobacterium butyricum* suspended in mineral oil 5 mg/ml). 20 Non-arthritic controls are injected with mineral oil. The animals are held for 2 weeks to allow development of arthritis. Paw volumes (uninjected, left hind paw) are measured and the adjuvant-injected rats are culled and distributed to treatment groups of 10 of equal disease severity. Non-arthritic controls are distributed to 2 groups of 10. The rats are given oral doses of compound or PVA-Acacia (Polyvinyl Alcohol 1%, Gum acacia, U.S.P. 5%, Methylparaben 0.5%) (10 ml/kg) by gavage on that day and on the 6 following days. One day after the last dose the paw volumes (uninjected, left hind paw) are measured using a Ugo Basile Volume Differential Meter Model 7101.

$$\frac{\text{Arthritic Control}}{\text{Mean Paw Volume (ml)}} - \frac{\text{Treatment Group}}{\text{Mean Paw Volume (ml)}} \times 100 =$$
$$\frac{\text{Arthritic Control}}{\text{Mean Paw Volume (ml)}} - \frac{\text{Non-Arthritic Control}}{\text{Mean Paw Volume (ml)}}$$

% Decrease from Control Mean Paw Volume.

Dose-response regression lines of the percent decrease are plotted on semi-log paper by visual fit and the ED50% decrease from control paw volume is determined by inspection. Data for some of the compounds in this invention are summarized in Table III.

Compounds from this series were also compared to indomethacin, phenylbutazone, ibuprofen, and aspirin.

PHENYLQUINONE WRITHING TEST

A standard procedure for detecting and comparing the analgesic activity of compounds in this series for which there is a good correlation with human efficacy is the standard phenylquinone writhing test modified from Siegmund, et al., *Proc. Soc. exp. Biol. Med.*, 95, 729 (1957). A test compound suspended in 1% methylcellulose was given orally to fasted (17–21 hours) female white mice, 5–20 animals per double blind test. Aqueous (0.01% phenyl-p-benzoquinone)phenylquinone, 0.20 ml per mouse, was injected intraperitoneally 6 minutes before observations were begun. At an appropriate time after the oral administration of the test compound, the mice were observed for 10 minutes for a characteristic stretching or writhing syndrome which is indicative of pain induced by phenylquinone. The effective analgesic dose for 50% of the mice ($ED_{50}$) was calculated by the moving average method of Thompson, W. R., *Bact. Rev.*, 11, 115–145 (1947); the time of peak activity was determined for many of the compounds. Data for some of the compounds is summarized in Table III together with data for some standard analgetic antiinflammatory drugs.

TABLE III
Biological Activity

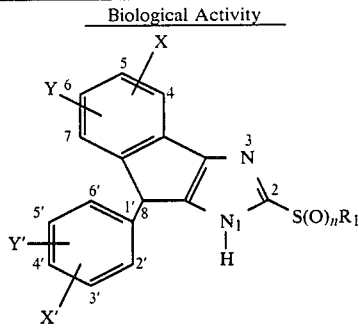

or

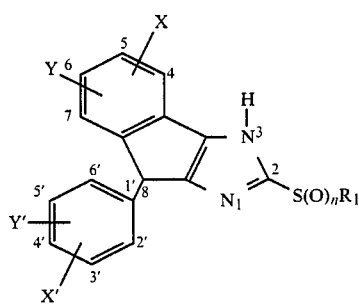

| Example | $R_1$ | n | X, Y X', Y' | Adjuvant Arthritic $ED_{50}$ (mg/kg) | Phenylquinone Writhing $ED_{50}$ (mg/kg) |
|---|---|---|---|---|---|
| 1 | $CF_2CHF_2$ | 0 | H | 0.79 | 0.16 |
| 2 | $CF_2CHF_2$ | 2 | H | 0.2 | 0.04 |
| 3 | $CF_3$ | 0 | H | 1.1 | 0.26 |
| 4 | $CF_3$ | 2 | H | 1.35 | 0.04 |
| 5 | $CF_3$ | 1 | H | 0.62 | 0.057 |
| 6 | $CH_3$ | 0 | H | 50 | 27 |
| 7 | $CH_3$ | 2 | H | 19 | 14 |

TABLE III-continued
Biological Activity

| Example | $R_1$ | n | X, Y X', Y' | Adjuvant Arthritic $ED_{50}$ (mg/kg) | Phenylquinone Writhing $ED_{50}$ (mg/kg) |
|---|---|---|---|---|---|
| 8 | $CF_3$ | 0 | 6-$OCH_3$ | 10.5 | 2.4 |
| 9 | $CF_3$ | 0 | 4-$OCH_3$ | >9 | 8.3 |
| 10 | $CF_3$ | 0 | 3,4-di-Cl | 44% @ 9[1] | 1.3 |
| 11 | $CH_2CH_3$ | 0 | H | 14 | 14 |
| 12 | $(CH_2)_3CH_3$ | 0 | H | >27 | 65 |
| 13 | $CF_3$ | 0 | 4'-$OCH_3$ | 3.2 | 0.147 |
| 14 | $CF_3$ | 2 | 4'-$OCH_3$ | 0.5 | 0.2 |
| 15 | $CF_2CHF_2$ | 0 | 5-$CH_3$ | 3.6 | 5 |
| 16 | $CF_2CHF_2$ | 2 | 5-$CH_3$ | 39% @ 9[1] | 0.064 |
| 17 | $CF_3$ | 0 | 4'-F | 2.4 | 0.14 |
| Indomethacin | | | | 0.3 | 0.35 |
| Phenylbutazone | | | | 10 | 80 |
| Ibuprofen | | | | 100 | 10 |
| Aspirin | | | | 305 | 135 |

[1]Paw volume reduction at indicated daily dose.

"Consisting essentially of" in the present disclosure is intended to have its customary meaning: namely, that all specified material and conditions are very important in practicing the invention but that unspecified materials and conditions are not excluded so long as they do not prevent the benefits of the invention from being realized.

What is claimed is:
1. A compound of the formula:

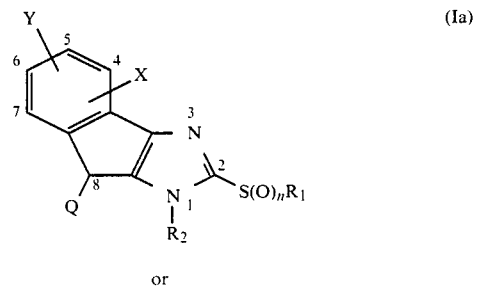

or

-continued

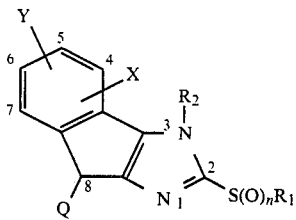
(Ib)

where
Q is

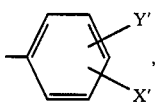

pyridyl or thienyl;
n is 0, 1 or 2;
$R_1$ is alkyl of 1 or 2 carbon atoms, or mono- or polyhaloalkyl of 1 or 2 carbon atoms;
$R_2$ is H, $C_1$–$C_6$ alkyl,

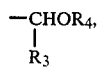

2-tetrahydropyranyl, 2-tetrahydrofuranyl, 4-nitrobenzyl, —$COOR_5$, —$COR_5$, —COAr or —$SO_2$Ar
where
$R_3$ is H or methyl;
$R_4$ is alkyl of 1–2 carbon atoms, benzyl, —$CH_2CH_2OCH_3$ or —$COR_5$;
$R_5$ is alkyl of 1–4 carbon atoms, or benzyl;
Ar is

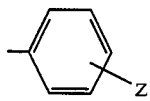

where Z is H, F, Cl, Br, alkyl of 1–4 carbon atoms, alkoxy of 1–4 carbon atoms or nitro; with the proviso that when $R_2$ is 4-nitrobenzyl, n is 2 and when $R_2$ is —$COOR_5$, —$COR_5$, —COAr or —$SO_2$Ar, n is 0;
X, Y, X' and Y' are independently H, F, Cl, Br, $NO_2$, alkoxy of 1 or 2 carbon atoms, —$N(C_{1-2}$ alkyl$)_2$, alkyl of 1 or 2 carbon atoms, —$S(O)_mC_{1-2}$ alkyl where m is 0, 1 or 2; or
a pharmaceutically suitable acid addition salt thereof when n is 0 or when X, Y, X' or Y' is —$N(C_{1-2}$ alkyl$)_2$ or when Q is pyridyl; or
a pharmaceutically suitable metal salt thereof when n is 1 or 2 and $R_2$=H.

2. A compound of claim 1 wherein Q is

$R_1$ is alkyl of 1 or 2 carbons or mono- or poly-fluoroalkyl of 1 or 2 carbons and $R_2$ is H.

3. A compound of claim 2 wherein n is 0 or 2.

4. A compound of claim 2 wherein $R_1$ is —$CF_3$ or —$CF_2CF_2H$.

5. A compound of claim 2 wherein X, Y, X', and Y' are independently H, F, Cl, —$OCH_3$ or —$CH_3$.

6. A compound of the formula:

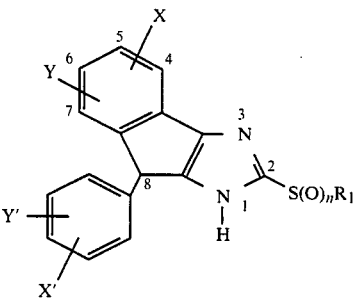
(IIa)

or

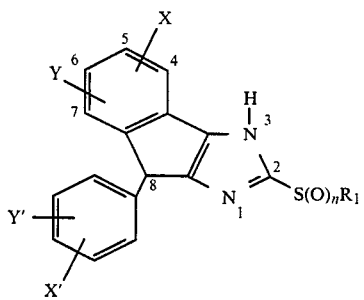
(IIb)

wherein
n is 0 or 2;
$R_1$ is —$CF_3$ or —$CF_2CF_2H$; and
X, Y, X' and Y' are independently H, F, Cl, —$OCH_3$ or —$CH_3$.

7. A compound of claim 6 wherein the X or Y substituent at the 4-position is H.

8. A compound of claim 6 wherein X, Y, X' and Y' are H.

9. The compound of claim 6 which is 1,8-dihydro(or 3,8-dihydro)-2-[(1,1,2,2-tetrafluoroethyl)-sulfonyl]-5-methyl-8-phenyl-indeno[1,2-d]imidazole.

10. The compound of claim 8 which is 1,8-dihydro(or 3,8-dihydro)-2-[(1,1,2,2-tetrafluoroethyl)thio]-8-phenyl-indeno[1,2-d]imidazole.

11. The compound of claim 8 which is 1,8-dihydro(or 3,8-dihydro)-2-[(1,1,2,2-tetrafluoroethyl)sulfonyl]-8-phenyl-indeno[1,2-d]imidazole.

12. The compound of claim 8 which is 1,8-dihydro(or 3,8-dihydro)-2-[(trifluoromethyl)thio]-8-phenyl-indeno[1,2-d]imidazole.

13. The compound of claim 8 which is 1,8-dihydro(or 3,8-dihydro)-2-[(trifluoromethyl)sulfonyl]-8-phenyl-indeno[1,2-d]imidazole.

14. A pharmaceutical composition for the treatment of inflammation, pain or both in a mammal consisting essentially of a suitable pharmaceutical carrier and an effective antiinflammatory or analgesic amount of at least one compound of claim 1 or claim 2 or claim 3 or claim 4 or claim 5 or claim 6 or claim 7 or claim 8 or claim 9 or claim 10 or claim 11 or claim 12 or claim 13.

15. A method of treating inflammation, pain or both in a mammal which comprises administering to the mammal an effective antiinflammatory or analgesic amount of at least one compound of claim 1 or claim 2 or claim 3 or claim 4 or claim 5 or claim 6 or claim 7 or claim 8 or claim 9 or claim 10 or claim 11 or claim 12 or claim 13.

* * * * *